United States Patent
Negi et al.

(10) Patent No.: US 10,293,153 B2
(45) Date of Patent: May 21, 2019

(54) PSEUDOPOROUS SURFACE OF IMPLANTABLE MATERIALS AND METHODS OF MAKING THE SAME

(71) Applicant: University of Utah Research Foundation, Salt Lake City, UT (US)

(72) Inventors: Sandeep Negi, Salt Lake City, UT (US); Rajmohan Bhandari, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 336 days.

(21) Appl. No.: 14/727,774

(22) Filed: Jun. 1, 2015

(65) Prior Publication Data
US 2015/0343204 A1 Dec. 3, 2015

Related U.S. Application Data (60) Provisional application No. 62/005,412, filed on May 30, 2014.

(51) Int. Cl.
*A61N 1/05* (2006.01)

(52) U.S. Cl.
CPC ......... *A61N 1/0551* (2013.01); *A61N 1/0529* (2013.01)

(58) Field of Classification Search
CPC ............................ A61N 1/0551; A61N 1/0529
(Continued)

(56) References Cited

U.S. PATENT DOCUMENTS

| 4,940,065 A | 7/1990 | Tanagho et al. |
| 5,321,334 A | 6/1994 | Kinoshita et al. |

(Continued)

FOREIGN PATENT DOCUMENTS

| JP | H09320610 A2 | 12/1997 |
| JP | 2000268827 A | 9/2000 |
| JP | 2007121636 A | 5/2007 |

OTHER PUBLICATIONS

Abidian et al, "Experimental and theoretical characterization of implantable neural microelectrodes modified with conducting polymer nanotubes", Biomaterials, Mar. 2008, 29(9): 1273-1283.
(Continued)

*Primary Examiner* — Nadia A Mahmood
(74) *Attorney, Agent, or Firm* — Thorpe North & Western, L.L.P (57) ABSTRACT

An implantable medical device can include an electrode substrate electrically connected to at least one electrode. The device can have a pseudoporous surface across the electrode substrate and electrode. This surface can result in a real surface area (RSA) greater than the geometric surface area (GSA) of the device. The pseudoporous surface can be a macroporous surface enabling a charge injection capacity greater than 1 mC/cm² while minimizing rejection of the device by surrounding tissue in chronic implant applications. The electrode can be a thin layer of conductive material, such as platinum or another metal, conformally deposited on the pseudoporous surface of the electrode substrate. A method of making the implantable device can include forming the device having an electrode substrate and at least one electrode electrically coupled to the electrode substrate, and forming a pseudoporous surface on the electrode substrate and electrode.

19 Claims, 4 Drawing Sheets

(58) Field of Classification Search
USPC .................................................. 607/116, 118
See application file for complete search history.

(56) References Cited

U.S. PATENT DOCUMENTS

| | | | |
|---|---|---|---|
| 6,034,295 A * | 3/2000 | Rehberg | A61B 17/72 433/201.1 |
| 6,103,319 A | 8/2000 | Harada et al. | |
| 7,571,011 B2 | 8/2009 | Zhou et al. | |
| 2007/0265692 A1 | 11/2007 | Koop et al. | |
| 2008/0140195 A1 | 6/2008 | Su et al. | |
| 2009/0143848 A1 | 6/2009 | Greenberg et al. | |
| 2009/0246515 A1 | 10/2009 | Negi et al. | |
| 2010/0010601 A1 | 1/2010 | Negi et al. | |
| 2011/0208031 A1 | 8/2011 | Wolfe et al. | |
| 2011/0311897 A1 | 12/2011 | Kato | |
| 2013/0090542 A1 | 4/2013 | Kipke et al. | |
| 2014/0114164 A1* | 4/2014 | Clark | A61N 1/0556 600/377 |
| 2015/0080906 A1* | 3/2015 | Fjorback | A61N 1/0558 606/129 |

OTHER PUBLICATIONS

Christensen et al, "The foreign body response to a penetrating, high density, silicon microelectrode array in the cat sciatic nerve", Biomaterials, In press.

Cogan, "Neural Stimulation and Recording Electrodes," *Annual. Review of Biomedical Engineering*, vol. 10, pp. 275-309, 2008.

Cogan, "Sputtered iridium oxide films(SIROFs) for neural stimulation electrodes",Conf Proc IEEE Eng Med Biol Soc., 2004, 6:4153-4156.

Edell et al, "Factors Influencing the Biocompatibility of insertable Silicon Microshafts in Cerebral Cortex," *IEEE Trans. Biomed, Eng.* vol. 39, pp. 635-643, 1992.

He et al, "Nanoscale Laminar Coating Modulates Cortical Scarring Response Around Implanted Silicon Microelectrode Arrays," *J. Neural Eng.*, vol. 3, pp. 316-326, 2006.

Heim et al, "Nanostructuration strategies to enhance microelectrode array (MEA) performance for neuronal recording and stimulation," *J. of Physiology-Paris*, doi:10.1016/j.jphysparis.2011.10.001, 2011.

Hochberg et al. "Neuronal ensemble control of prosthetic devices by a human with tetraplegia," *Nature*, vol. 442, pp. 164-17, 2006.

Klein et al, "Morphology and charge capacity of sputtered iridium oxide films", JVSTA, 1989, 6 pages.

Ludwig et al, "Chronic neural recordings using silicon microelectrode arrays electrochemically deposited with a poly(3,4-thylenedioxythiophene) (PEDOT) film," *J. Neural. Eng*, vol. 3, pp. 59-70, 2006.

McCreery et al, "Charge density and charge per phase as cofactors in neural injury induced by electrical stimulation," *IEEE Trans. Biomed. Eng.* vol. 37, pp. 996-1001, 1990.

McKenzie et al, "Decreased Functions of Astrocytes on Carbon Nanofiber Materials," *Biomaterials*, vol. 25, pp. 1309-1317, 2004.

Merrill et al, "Electrical Stimulation of Excitable Tissue: Design of Efficacious and Safe Protocols," *J. Neurosci Methods*, vol. 141, pp. 171-198, 2005.

Moxon et al, "Bioactive properties of Nanostructured Porous Silicon for Enhancing Electrode to Neuron Interfaces," *J. Biomater. Sci. Polym. Ed*,18, pp. 1263-1281, 2007.

Moxon et al, "Nanostructured Surface Modification of Ceramic Based Microelectrodes to Enhance Biocompatibility for a Direct Brain Machine Interface," *IEEE Trans. Biomed. Eng*, vol. 51, pp. 881889, 2004.

Negi et al, "Effect of sputtering pressure on pulsed-DC sputtered iridium oxide films", Department of Electrical and Computer Engineering, University of Utah, 2008, 9 pages.

Negi et al, "In vitro comparison of sputtered iridium oxide and platinum coated neural implantable microelectrode arrays," *Biomedical Materials*, vol. 5, No. 1, 2010.

Negi et al, "Neural electrode degradation from continuous electrical stimulation: comparison and activated iridium oxide," *Journal of Neuroscience Methods*, vol. 186, pp. 8-17, 2010.

Normann, "Technology Insight: future neuroprosthetic therapies for disorders of the nervous system," *Nature Clinical Practice: Neurology*, vol. 3, No. 8, pp. 444-452, 2007.

Skousen et al, "Reducing surface area while maintaining implant penetrating profile lowers the foreign body response to chronically implanted planar silicon microelectrode arrays", Progress in Brain Research, 2011;194:167-80.

Slavcheva et al, "Sputtered Iridium Oxide Films as Charge Injection Material for Functional Electrostimulation", Journal of the Electrochemical Society, 2004, 151(7), pp. E226-E237.

Venkatraman et al, "In Vitro and In Vivo Evaluation of PEDOT Microelectrodes for Neural Stimulation and Recording", IEEE Transactions on Neural systems and Rehabilitation Engineering, Jun. 2011, vol. 19, No. 3, 10 pages.

Wang, "A Carbon Nanotube Microelectrode Array for Neural Stimulation", Dissertation, Jun. 2006, 173 pages.

Winslow et al, "A comparison of the tissue response to chronically implanted Parylene-C-coated and uncoated planar silicon microelectrode arrays in rat cortex", Biomaterials, Dec. 2010;31(35):9163-72.

Winslow et al, "Quantitative analysis of the tissue response to chronically implanted microwire electrodes in rat cortex", Biomaterials. Mar. 2010;31(7):1558-67.

Yao et al, "Micro Multi-Probes Electrode Array for the Recording Retinal Neuron Signal", Solid-State Sensors, Actuators and Microsystems Conference, Jun. 2007, pp. 1373-1376.

* cited by examiner

PSEUDOPOROUS SURFACE OF IMPLANTABLE MATERIALS AND METHODS OF MAKING THE SAME

RELATED APPLICATION(S)

This application claims the benefit of Provisional Application No. 62/005,412, filed May 30, 2014, which is incorporated by reference in its entirety.

GOVERNMENT INTEREST

This invention was made with government support under R43 NS073162 awarded by the National Institutes of Health. The government has certain rights in the invention.

FIELD OF THE INVENTION

This invention relates to implantable medical devices having exposed surfaces modified to increase surface area before adherent, conformal, thin films are applied. Accordingly, the invention involves the fields of medical device technology, biological chemistry, electrical engineering, physics, and materials science.

BACKGROUND

Potential for extending long term use of implantable medical devices increases with continual innovations extending battery life. As battery life improves, improvements continue to be sought to enable implantable medical devices to sustain functional efficiency over an extended device lifetime and increase chronic biocompatibility. Longevity of implantable medical devices with electrodes is often limited by glial encapsulation. Glial cells are non-neuronal cells that provide support and protection for neurons in the brain and peripheral nervous system. Implanting a medical device near a neuron can trigger glial encapsulation, which is a biological response that forms glial scar tissue around the medical device. Glial encapsulation creates a slowly, but continuously, growing impedance barrier that requires increased charge flow to overcome. Unfortunately, such glial encapsulation also progressively weakens the electrode signal, and physically displaces the implant, causing the implant to move away from the original implant location.

SUMMARY

An implantable medical device can include an electrode substrate and at least one electrode electrically connected to the electrode substrate. The device can have a pseudoporous surface across the electrode substrate and the electrode.

A method of making an implantable medical device can include forming the device having an electrode substrate and at least one electrode electrically coupled to the electrode substrate. The method can also include forming a pseudoporous surface on the electrode substrate and the electrode.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "an electrode" includes reference to one or more electrodes and reference to "etching" refers to one or more such steps.

As used herein, "RMS roughness" is a measure of surface micro-roughness or nano-roughness referring to a root mean square of micron or nanometer scale height measurements made in a repeatable rastering pattern over a defined surface area and calculated according to $$R_{rms} = \sqrt{\frac{\sum_{n=1}^{N}(z_n - \bar{z})^2}{N-1}}$$

where $z_n$ is a height difference between the lowest point on a sampled plane, and a point presently sampled, n identifies a singular measurement of a series, each made at a unique location on the sample, and N represents a total number of height measurements.

As used herein, "Geometric Surface Area (GSA)" refers to the area of the surface which can be determined with ordinary tools designed to measure a length as the geometric surface area boundaries and as the projection of the real surface on a plane parallel to the macroscopic, visible phase boundary. Thus, GSA is calculated on the basis of known geometric dimensions of the object and whose resolution is normally that of macroscopic measurements.

As used herein, "Real Surface Area (RSA)" refers to the area of the surface defined by microscopic asperities. Only for liquids does the real surface area coincide with the geometric surface area. In the case of solids, asperities are present whose height may be orders of magnitude greater than the atomic or molecular size, though lower than visible resolution. Thus, the RSA is higher than GSA and experimental data can be normalized to the real surface area to become universally comparable. The RSA per unit geometric surface area is also the roughness factor, fr=[GSA]/[RSA].

As used herein, "pseudoporous" is used to differentiate from "porous electrodes" that are formed using sputter deposition or similar deposition methods that create porous surfaces with small pores between grains or platelets of the deposited material. Pseudoporous surfaces have larger pores that extend deeper into the surface compared to such porous surfaces, and is accordingly formed of wells rather than through-holes.

As used herein, "macroporous" refers to a surface having pores of a particular size range. Macropores are cavities that are larger than 50 nm in diameter. Macroporous materials have larger pores than mesoporous (2-50 nm) and microporous (0.2-2 nm) materials.

As used herein, "conformal" and "conformally" refers to a characteristic of a thin layer formed on a pseudoporous surface, in which the thin layer follows surface contours of individual pores in the pseudoporous surface. If a thin layer is conformally deposited on a pseudoporous surface, then the thin layer can have a roughly uniform layer thickness covering the interior surfaces of pores in the pseudoporous surface, although the layer thickness can vary in some cases. The thin layer can have a layer thickness small enough so that the thin layer can cover interior surfaces of a pore without substantially filling the interior volume of the pore. It is to be understood that a pseudoporous surface can have a range of pore sizes, so that some of the smallest pores may be so small that the thin layer substantially fills these pores. However, a significant portion of the pores can be large enough that the thin layer coats the inside surfaces of the pores without filling the pores. In some cases, a majority of the pores in the pseudoporous layer by total volume of pores can have interior surfaces coated by the thin layer without being filled by the thin layer.

As used herein, "pore depth" refers to the distance from the geometric surface to the deepest point in a pore. The geometric surface is typically the outermost plane at which solid material making up a pseudoporous surface is present. The pores extend into the geometric surface to a pore depth. As used herein, "average pore depth" refers to a number average unless otherwise stated.

As used herein, "impedance" refers to impedance at 1 kHz unless state otherwise.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, pressures, flow rates, deposition rates, material properties, electrical performance data, power values, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Pseudoporous Surface of Implantable Materials

One surface property which can be modified to reduce glial encapsulation is the ratio of real surface area (RSA) to geometric surface area (GSA) of the implantable electrode device. A surface that exhibits increased RSA/GSA in substantially all implantable areas of the device, not limited to the electrically active portions, can reduce glial encapsulation in multiple ways. A larger RSA/GSA provides a larger surface area for biointegration with the subject tissue, with a porous structure providing bonding surfaces with depth and facing in multiple directions, better securing the device against physical forces that would break those bonds. Additionally, increasing RSA/GSA reduces astrocyte adhesion around the electrode, including hypertrophied astrocytic cell bodies from which glial scars are grown. Most notably, increasing RSA/GSA reduces the initial value of the impedance of the electrode.

Impedance is a function of real surface area of the electrically active portion of the electrode, and increasing RSA/GSA provides electrodes with lower impedance upon implantation than a smooth-surfaced electrode. The process of glial encapsulation creates a growing thin film of non-conductive scar tissue at the interface between the implanted device and surrounding undisturbed tissue. Not only does this progressively distance the electrode from its target site and progressively dampen the signal amplitude, but also continuously increases electrode impedance, which must be overcome in order for the electrode device to maintain function. Overcoming the increasing impedance typically involves increasing charge injection at the electrically active site of the electrode. Increasing charge injection accelerates irreversible electrochemical reactions at the interface, oxidizing saline, oxidizing organics, causing some electrode material to dissolve and oxidize, and producing chemical species that may be damaging to the tissue, accelerating biological rejection. Voltage across the interface is closely monitored and kept within certain safety limits to avoid introducing unacceptable chemical damage levels and, in the extreme, exceeding the water window, the potential at which local electrolysis is initiated, producing $H_2$ and $O_2$ vapor. Changes in injection current density at the electrode, monitored over time, present a method to indirectly measure the electrochemical contribution to tissue damage and track and predict implantable electrode device lifetime. When the implanted electrode device surface is pseudoporous, the RSA/GSA is sufficiently large that the impedance of the electrode at the time of implantation is significantly smaller than the impedance would have been with a smooth surface, significantly extending the time for glial scar growth to increase impedance beyond a maximum safe threshold.

The maximum charge that can be injected by an implanted electrode device without polarizing the electrode beyond the potential for electrolysis is termed the Charge Injection Capacity (CIC). For the efficacy of stimulating electrodes, a high CIC is desired, and it has been reported that a current threshold of at least 20mC/cm2 can in some cases be required to evoke responses in human applications. CIC is material- and geometry-dependent. Use of a material with good biocompatibility and high CIC, conformally deposited in a thin film over a substrate previously treated to be pseudoporous, can provide a combination of low glial encapsulation rate, low initial impedance, and high CIC, maximizing the longevity of the implanted electrode device.

Accordingly, an implantable medical device can include an electrode substrate electrically connected to at least one electrode. The surfaces of at least half, and in some cases substantially all, areas of the electrode(s) and substrate can be pseudoporous. Such surfaces result in a real surface area (RSA) substantially greater than the geometric surface area (GSA) of the device. The pseudoporous surface can be a macro-porous surface enabling a charge injection capacity greater than 1 $mC/cm^2$ while minimizing rejection of the device by surrounding tissue in chronic implant applications. In some cases the charge injection capacity can be greater than 10 $mC/cm^2$, and in another aspect greater than 20 $mC/cm^2$, and in yet another aspect up to about 50 $mC/cm^2$. Non-limiting examples of implantable medical devices for which this unique pseudoporous surface can advance performance parameters such as charge injection capacity and tissue rejection rates include a Utah Electrode Array (UEA), a cochlear implant, an EKG electrode, a deep brain stimulation device, a neural device, a pacemaker, and other peripheral or central nervous system stimulation devices. The present invention can be applied to cortical stimulation and recording, deep brain stimulation, cardiac pacing, pain management, and other applications.

Figure 1:
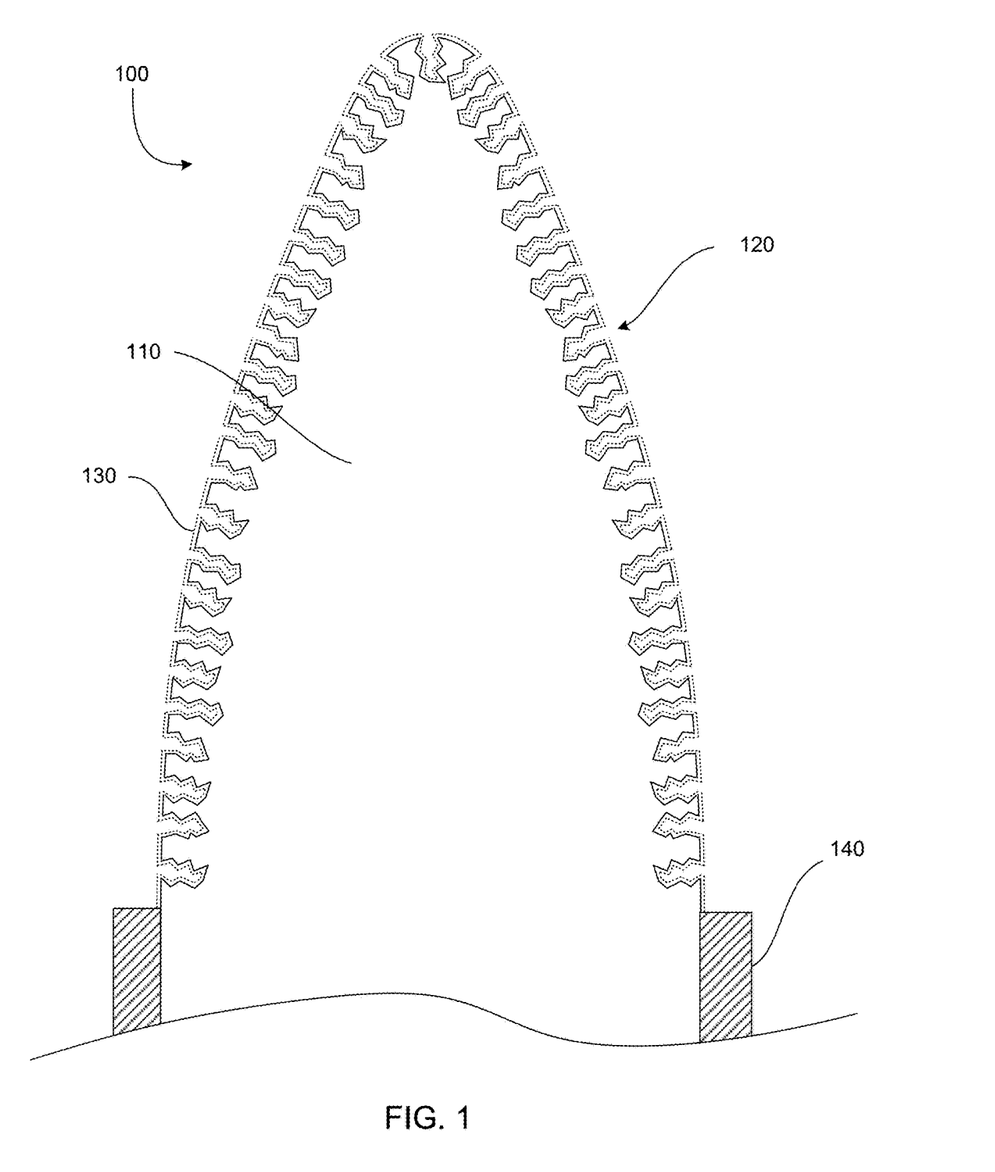
FIG. 1 is a cross-section of a portion of an implantable medical device in accordance with an embodiment of the present invention.

FIG. 1 shows an example of a portion of an implantable device 100. In the embodiment shown, the device is shaped as a needle for puncturing a target tissue. The device includes an electrode substrate 110 making up a core portion of the device. The electrode substrate has pores 120 etched into the surface of the electrode substrate at the tip of the device. This gives the electrode substrate a pseudoporous surface. After etching the pores, an electrode 130, indicated in FIG. 1 by a dotted line, is deposited as a thin layer of conductive material conforming to the pseudoporous surface of the electrode substrate. As shown in the figure, the thin layer of conductive material conforms to the interior surfaces of the pores, so that the conductive material does not fill the interior volume of the pores. Thus, the final surface after depositing the electrode is still pseudoporous. The device also includes an insulating layer 140 around the needle shaft. In some embodiments, the insulating layer can also have a pseudoporous surface to improve biocompatibility. Additionally, in some embodiments, the electrode layer can continue along the shaft of the device beneath the insulating layer. Alternatively, the electrode layer can be deposited only at the uninsulated tip of the device.

Figure 2A:
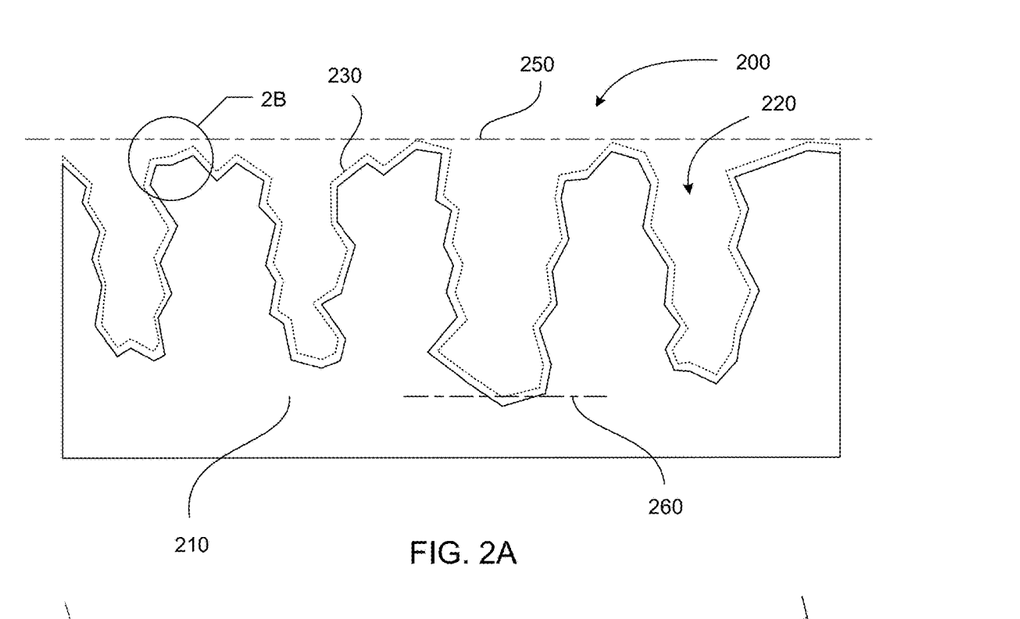
FIG. 2A is a close-up view of a pseudoporous surface in accordance with an embodiment of the present invention.

FIG. 2A shows a close-up view of another example of a pseudoporous surface 200. The pseudoporous surface is formed from an electrode substrate 210 with pores 220 etched into its surface. An electrode 230 is conformally deposited on the pseudoporous surface. The geometric surface 250 is represented by a dotted and dashed line. This surface may be visible to the naked eye and measurable with conventional measuring tools. The pores extend from the geometric surface down to a pore depth 260. The pores can have varying pore depths, so that the pores taken together have an average pore depth.

Figure 2B:
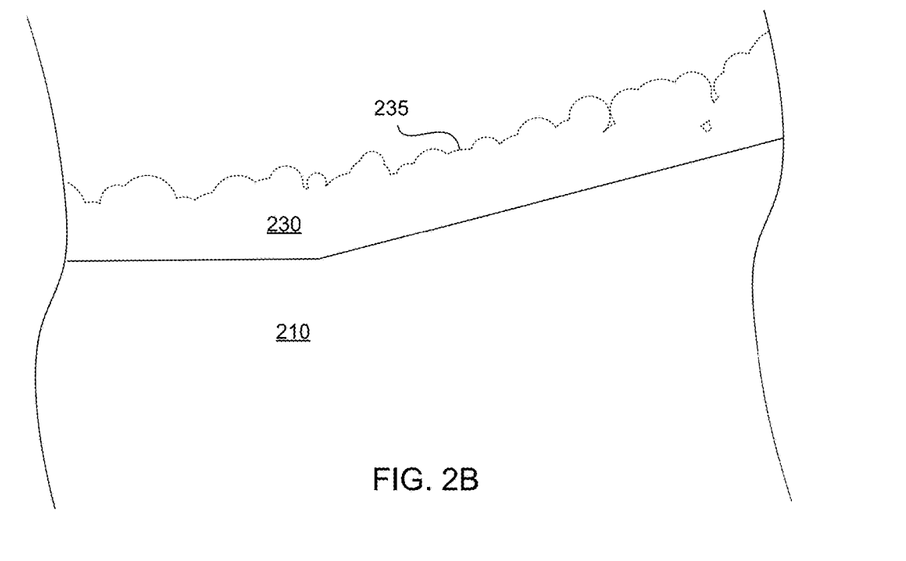
FIG. 2B is a closer view of the circled portion from FIG. 2A.

FIG. 2B shows a closer view of the circled portion of FIG. 2A. The interface between the electrode substrate 210 and the electrode 230 is shown. This closer view shows the microporous surface 235 of the electrode. This type of surface can be formed by deposition processes such as sputtering. FIG. 2B shows the difference in scale between the microporous surface and the pseudoporous surface shown in FIG. 2A. The pseudoporous surface provides more additional surface area for reducing impedance, increasing charge injection, and increasing biocompatibility. Other methods of depositing the electrode material, besides sputtering, can be used and can form electrodes with surfaces that are smoother or rougher than the microporous surface shown in FIG. 2B.

It should be noted that the pseudoporous surfaces shown in FIGS. 1, 2A, and 2B are idealized depictions. In practice, the pores of a pseudoporous surface can vary drastically in size and shape and can generally be less ordered that the pores shown in the figures. The pores shown in the figures may also not be to scale. Therefore, pore sizes, pore depths, layer thicknesses, and the like are described in this description and not to be inferred from the figures.

The roughness of the pseudoporous surface can be imaged using Scanning Electron Microscopy (SEM) and/or Atomic Force Microscopy (AFM). AFM is notably capable of characterizing surface topography on a sub-micron scale, including roughness of a pseudoporous surface. The roughness of a pseudoporous surface can be quantified as a root mean square (RMS) of height measurements. Roughness measurements can be performed and recorded by AFM. In some embodiments, the RMS roughness can be from about 10 to about 60 nanometers. Pore depths of the pseudoporous surface can be measured and recorded using SEM or AFM as well.

In some embodiments, the pseudoporous surface can have pores with pores depths from about 1 μm to about 15 μm, and in some cases up to 10 μm. Although pore depths can vary over a wide range, in some embodiments the pseudoporous surface can have an average pore depth from about 1 μm to about 10 μm. In further embodiments, the pores can have widths of from about 100 nm to about 10 μm. In some cases, the pores can have an average pore width from about 500 nm to about 5 μm.

The layer of conductive material forming the electrode can be sufficiently thin to conform to the pseudoporous surface of the electrode substrate without substantially filling the pores. In some cases, the layer of electrically conductive material can have a layer thickness of less than half the average pore width. In further cases, the layer of electrically conductive material can have a layer thickness of less than 20% or less than 10% of the average pore width. In some embodiments, the layer of electrically conductive material can have a layer thickness of from about 50 nm to about 5 μm. The layer thickness can be substantially uniform over the pseudoporous surface, or the layer thickness can vary somewhat such as varying within 10% of an average layer thickness, varying within 20% of an average layer thickness, or varying within 50% of an average layer thickness. In some embodiments, the layer of electrically conductive material can have a microporous or mesoporous surface. In other embodiments, the layer of electrically conductive material can have smooth surface that conforms to the pseudoporous surface of the electrode substrate.

Figure 3:
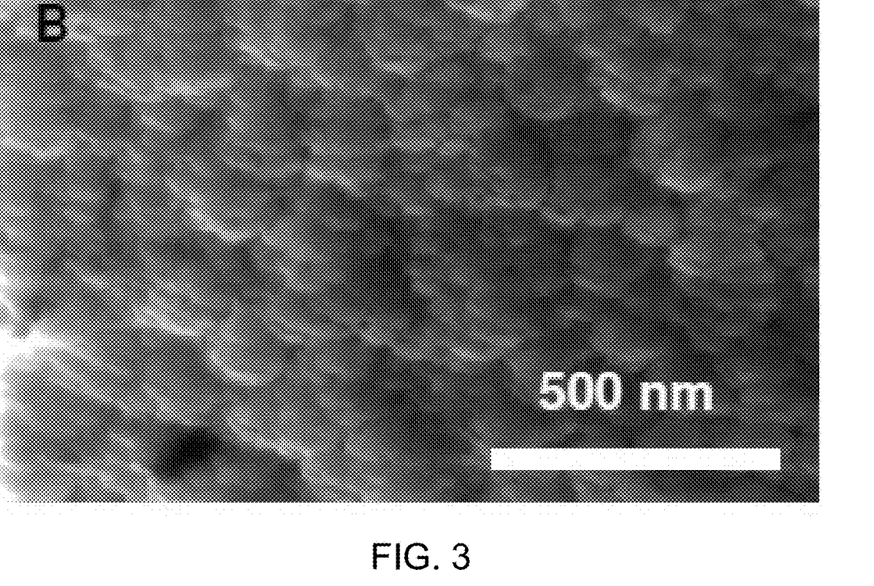
FIG. 3 is an SEM micrograph of platinum showing a dense microstructure.
Figure 4:
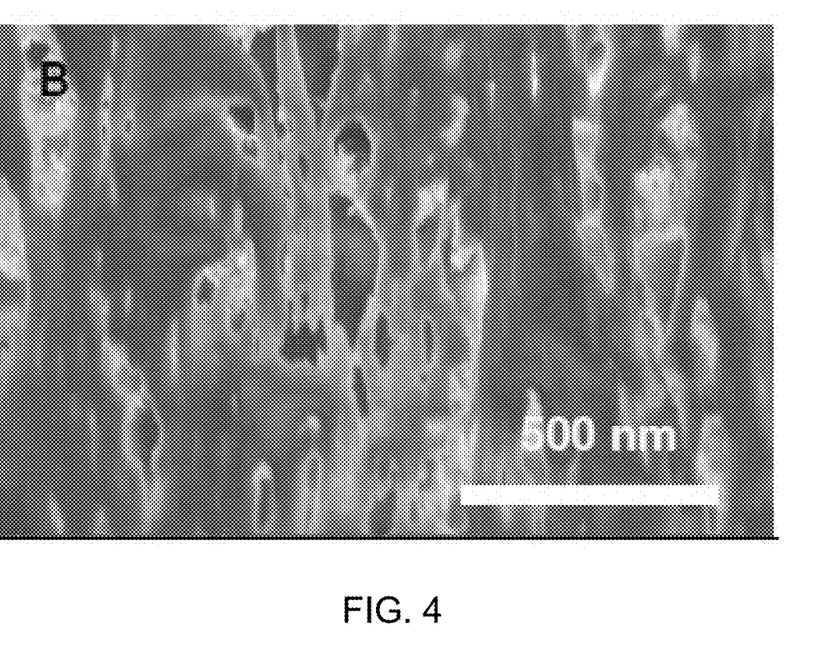
FIG. 4 is an SEM micrograph of a pseudoporous surface in accordance with an embodiment of the present invention.

FIG. 3 is an SEM micrograph of a platinum microporous surface. This is an example of a surface that is not pseudoporous and does not have the same biocompatibility and charge transfer characteristics as a pseudoporous surface. FIG. 4 is an SEM micrograph of a pseudoporous surface in accordance with embodiments of the present invention. A comparison between these figures shows that the pseudoporous surface has larger and deeper pores, which provides better biocompatibility, lower impedance, and higher CIC than the microporous surface.

Although other materials can be used, the electrode(s) can be formed of platinum. Other suitable electrode materials can include, but are not limited to, iridium, iridium oxide, platinum-iridium, tantalum, tantalum-tantalum oxide, gold, titanium nitride, carbon nanotubes, conducting polymer such as PEDOT, and the like. At least one electrode can include an exposed electrical contact and remaining portions of the implantable device can be coated with an electrically insulative material.

Fabricating the implantable medical device can begin by forming an electrode substrate with the geometric structure desired to position and support the electrically active electrode site(s) which can be electrically coupled to the electrode substrate. The surface of the resulting geometric structure can also be made pseudoporous. A variety of methods can be used to form the pseudoporous surface in the electrode substrate. In some embodiments, the pseudoporous substrate can be formed by: Reactive Ion Etching (RIE), deep reactive ion etching (DRIE), sputtering, focused ion beam (FIB) etching, XeF2 etching, sand blasting, wet chemical etching, Metal-Organic Chemical Vapor Deposition (MOCVD), Low Pressure Chemical Vapor Deposition (LPCVD), Atmospheric Pressure CVD (APCVD), Ultra High Vacuum CVD (UHVCVD), Direct Liquid Injection CVD (DLICVD), Microwave Plasma assisted CVD (MP-CVD), Plasma Enhanced CVD (PECVD), Atomic Layer CVD (ALCVD), hot filament CVD (HFCVD) Hybrid Physical-Chemical Vapor Deposition (HPCVD), Rapid Thermal CVD (RTCVD), hot-wall CVD, Vapor Phase Epitaxy (VPE), aerosol assisted CVD (AACVD), polymerization of siloxanes attached to the starting substrate surface, electrochemical deposition of a silicide, or Stranski-Krastanov (SK) or Volmer-Weber (VW) epitaxial growth of materials of substantial lattice mismatch, potentially SiC on Si or diamond on Si. In one particular embodiment, the pseudoporous surface can be formed by reactive ion etching.

The electrode substrate can be formed from a variety of materials. In certain embodiments, electrically conductive, semiconductive, or nonconductive materials can be used. For example, the electrode substrate can include silicon, silicon dioxide, silicon nitride, platinum, iridium, gold, platinum-iridium, iridium oxide etc. In one embodiment, the electrode substrate can be silicon.

A thin film of electrically conductive material can be deposited on the pseudoporous surface of the electrode substrate. Focused Ion Beam (FIB) deposition, sputtering, (DC, RF or pulsed DC), e-beam evaporation, electrochemical, electroplating, electroless plating, or chemical vapor deposition (CVD) can enable a pattern to be deposited and electrical connection to the electrode substrate be made in a single deposition step.

Material choice and surface microstructure can affect the safe and efficient function of implantable medical electrode devices in chronic applications. A large ratio of Real Surface Area (RSA) to Geometric Surface Area (GSA) can facilitate biocompatibility, reduce the rate of glial encapsulation, and extend the safe operating lifetime of the device. In some embodiments, substantially the entire surface of the device can have the large ratio of RSA to GSA. In other embodiments, at least a majority of the surface can have the large ratio of RSA to GSA. In still other embodiments, at least the electrodes of the device can have the large ratio of RSA to GSA.

Electrode materials with high Charge Injection Capacity (CIC) can allow for minimizing electrode size. Smaller electrodes can achieve higher stimulation current density while operating within safe voltage limits that avoid gas evolution by electrolysis or electrochemical reactions. Furthermore, higher CIC lowers the potential required for stimulation, which can reduce injury and glial encapsulation at the stimulation site. Minimizing electrode size can also improve spatial resolution and selectivity of the implantable electrode device. However, charge injection decreases as the surface area of the electrode decreases, increasing the electrode impedance, and reducing its sensitivity. As a result, there is a tradeoff between selectivity and sensitivity. The present invention can be used to overcome this design constraint through surface modification, rendering an initially smooth surface pseudoporous to increase RSA without changing GSA.

In some embodiments of the present invention, the RSA/GSA of the underlying substrate can be modified and a high RSA/GSA can be maintained over all treated areas after electrically conductive material is conformally deposited over selective areas. Thus, the substrate and the electrically conductive material can have a pseudoporous surface. The porosity of the pseudoporous surface can be optimized without thin film constraints, and serves in both electrically active and electrically inert areas to improve biointegration and device longevity as compared to implantable devices with smooth surfaces. Accordingly, a thick substrate of greater than 1 μm, in some cases greater than 8 μm, and in some cases greater than 13 μm can be used to make pseudoporous surfaces which are not limited to typical 1 μm depth.

The pseudoporous surfaces according to the present invention can increase the RSA of the electrode without altering the GSA to achieve better stimulating and recording electrode characteristics. The present invention can provide more improved characteristics than previously available thin film deposition methods. Previous methods have obtained different degrees of porosity, roughness and thickness of electrode material by different coating methods (electrode-position, sputtering, etc.) and process parameters (deposition pressure, substrate bias and temperature, gas composition and flow rate etc.). However, the thickness of these electrode materials is typically less than 1 μm owing to the growing thin film residual stress and adhesion concerns of the material to the underlying substrate. Hence, the RSA defined by the surface morphology and degree of porosity/roughness is limited in range due to the limited thickness of the deposited film/electrode material. As a result there is a limit to the achievable CIC. FIG. 3 illustrates a typical metal film deposited on an electrode surface, while Table 1 lists CIC for various electrode materials.

TABLE 1

| Material | Mechanism | CIC (mC/cm$^2$) |
|---|---|---|
| Pt | Faradaic | 0.05-0.15 |
| AIROF | Faradaic | 1-5 |
| TIROF | Faradaic | 1 |
| SIROF | Faradaic | 1-5 |
| Ta/Ta$_2$O$_5$ | Capacitive | 0.5 |
| TiN | Capacitive | 1 |
| PEDOT | Faradaic | 15 |

In contrast, the approach of the present invention modifies the actual electrode substrate (e.g. silicon in Utah Electrode Array) itself. The thickness of the electrode substrate can vary from sub-micrometer to 50 μm, typically. The electrode substrate can be modified to have pores extending multiple micrometers below the surface. Thus, the greater thickness of the electrode substrate can potentially allow for more increase in RSA compared to the previously available thin film methods that may be limited to 1 μm or less. Furthermore, in the present approach the surface modified electrodes can be coated by metal through conformal deposition. The resulting pseudoporous electrode can have superior electrochemical characteristics. FIG. 4 shows a pseudoporous electrode surface in accordance with the present invention. Table 2 illustrates various properties of an exemplary Utah Electrode Array modified as outlined above.

TABLE 2

| | CSC mC/cm$^2$ | CIC mC/cm$^2$ | Impedance (@ 1 kHz) |
|---|---|---|---|
| Surface Modified Utah Array | 3000 | 24 | 186 Ω |

The pseudoporous electrodes of the present invention can be less dense than previously available metal film electrodes. In the denser metal film electrodes, only the outer parts of the film are accessed at high frequency, limiting the CIC of the material. Metal surfaces within the deeper layers do not contribute to the CIC due to the long RC time constant at high frequency of the deeper layers. FIG. 3 illustrates a typical dense electrode material coated on an electrode substrate. The thin film microstructure is dense and as a result the pore resistance is high.

In contrast, in the approach herein the entire microstructure comprised of the electrode substrate conformally overcoated with conductive material contributes towards increasing the CIC and decreasing the impedance. The macrostructure formed in the substrate is highly porous and the conductive material is conformally coated. FIG. 4 is an SEM micrograph of such a pseudoporous structure.

Figure 5:
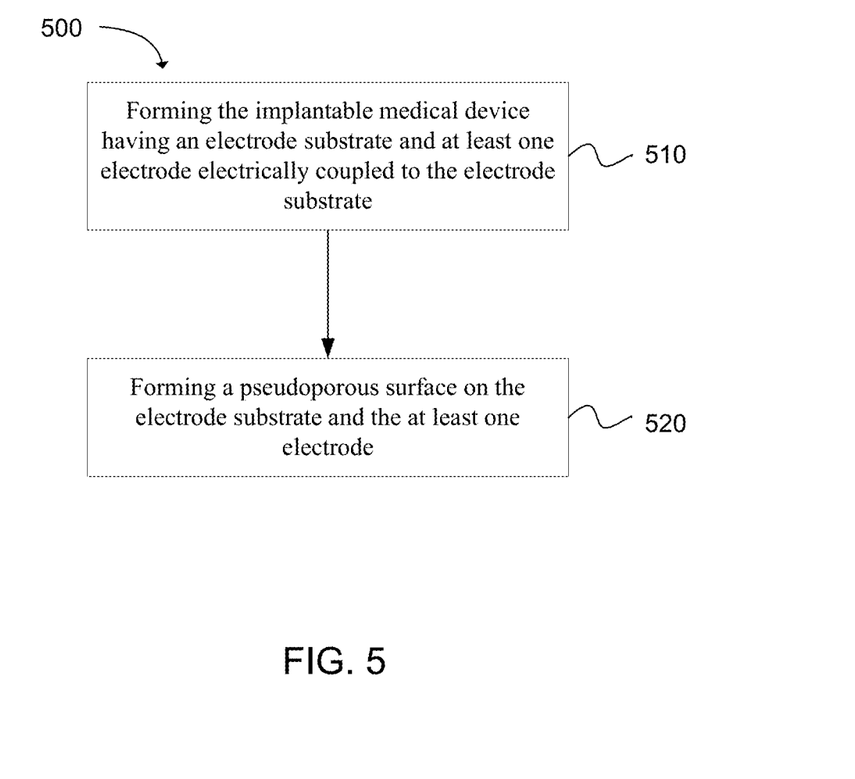
FIG. 5 is a flowchart of a method of making an implantable medical device in accordance with an embodiment of the present invention.

The present invention also extends to methods of making implantable medical devices. FIG. 5 is a flowchart of one embodiment of a method 500 for making an implantable medical device. The method includes forming the implantable medical device having an electrode substrate and at least one electrode electrically coupled to the electrode substrate 510, and forming a pseudoporous surface on the electrode substrate and the at least one electrode 520.

Methods of making the implantable medical devices can include steps to achieve any of the characteristics and properties of the devices described herein. Thus, it should be noted that any properties and characteristics described herein with respect to embodiments of implantable medical devices can also be applied to embodiments of methods for making the implantable medical devices. Likewise, any method steps described herein can be applied to embodiments of the implantable medical devices.

In some embodiments, a method of making an implantable medical device can include first forming an electrode substrate. The electrode substrate can be formed in the desired geometric shape of the final device. After forming an electrode substrate with the desired shape, surfaces of the electrode substrate can be modified to be pseudoporous. In certain embodiments, this can be achieved by etching the surface. In one particular embodiment, the pseudoporous surface can be formed by reactive ion etching (RIE). In another embodiment, the pseudoporous surface can be formed by wet chemical etching. After forming a pseudoporous surface, a layer of electrically conductive material can be deposited on the pseudoporous surface. The layer of electrically conductive can be deposited so that the layer conforms to the pseudoporous surface. Any of the deposition methods described herein can be used to deposit the layer of electrically conductive material. In one particular embodiment, the layer of electrically conductive material can be deposited using focused ion beam (FIB) deposition. The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. An implantable medical device comprising:
   a) an electrode substrate having a pseudoporous surface;
   b) at least one electrode electrically connected to the electrode substrate, wherein the electrode is a layer of electrically conductive material conforming to the pseudoporous surface of the electrode substrate such that the electrode also has the pseudoporous surface.

2. The device of claim 1, wherein a real surface area (RSA) of the pseudoporous surface is greater than a geometric surface area (GSA) of the pseudoporous surface.

3. The device of claim 2, wherein the RSA is from 2 to 100 times greater than the GSA.

4. The device of claim 1, wherein a roughness of the pseudoporous surface is root mean square (RMS) of height measurements, wherein the RMS is from 10 to 60 nanometers.

5. The device of claim 1, wherein the pseudoporous surface has pore depths from about 1 μm to about 10 μm.

6. The device of claim 1, wherein the pseudoporous surface has an average pore width from about 500 nm to about 5 μm.

7. The device of claim 1, wherein the pseudoporous surface is a macro-porous surface having a charge injection capacity greater than 1 mC/cm$^2$.

8. The device of claim 1, wherein the pseudoporous surface is a macro-porous surface having a charge injection capacity greater than 10 mC/cm$^2$.

9. The device of claim 1, wherein the pseudoporous surface is a macro-porous surface having a charge injection capacity greater than 20 mC/cm$^2$.

10. The device of claim 1, wherein the layer of electrically conductive material has a thickness from about 50 nm to about 1 μm.

11. The device of claim 1, wherein the at least one electrode is formed of platinum.

12. The device of claim 1, wherein the at least one electrode includes an exposed electrical contact and remaining portions of the implantable device are coated with an electrically insulative material.

13. The device of claim 1, wherein the pseudoporous surface covers substantially all surfaces of the electrode substrate and the at least one electrode.

14. The device of claim 1, wherein the pseudoporous surface covers at least 50% of surfaces of the electrode substrate and the at least one electrode.

15. The device of claim 1, wherein the implantable device is selected from the group consisting of a Utah electrode array, a cochlear implant, an EKG electrode, and a pacemaker.

16. The device of claim 1, wherein the implantable device is a Utah electrode array.

17. The device of claim 1, wherein the pseudoporous surface is formed by etching the electrode substrate, then conformally depositing the electrode on the etched electrode substrate.

18. The device of claim 1, wherein the electrode substrate comprises silicon.

19. The device of claim 1, wherein the device is shaped as a needle.

* * * * *